US010877030B2

(12) United States Patent
Schraeml et al.

(10) Patent No.: US 10,877,030 B2
(45) Date of Patent: Dec. 29, 2020

(54) VELOCITY FACTOR (71) Applicant: Hoffmann-La Roche Inc., Little Falls, NJ (US)

(72) Inventors: Michael Schraeml, Penzberg (DE); Leopold Von Proff, Hohenpeissenberg (DE)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 15/287,453

(22) Filed: Oct. 6, 2016

(65) Prior Publication Data

US 2017/0212107 A1 Jul. 27, 2017

Related U.S. Application Data (60) Division of application No. 14/090,456, filed on Nov. 26, 2013, now Pat. No. 9,488,661, which is a continuation of application No. 13/392,217, filed as application No. PCT/EP2010/062115 on Aug. 19, 2010, now Pat. No. 8,617,849.

(30) Foreign Application Priority Data

Aug. 25, 2009 (EP) .................................... 09010844

(51) Int. Cl.
*G01N 33/68* (2006.01)
*C07K 16/00* (2006.01)
*C07K 16/46* (2006.01)
*G01N 33/557* (2006.01)

(52) U.S. Cl.
CPC ........... *G01N 33/557* (2013.01); *C07K 16/00* (2013.01); *C07K 16/461* (2013.01); *G01N 33/6854* (2013.01); *C07K 2317/24* (2013.01); *C07K 2317/90* (2013.01); *C07K 2317/92* (2013.01); *C07K 2317/94* (2013.01)

(58) Field of Classification Search
CPC ............. G01N 33/557; G01N 33/6854; G01N 2015/0003; G01N 21/553; G01N 2021/5903; C07K 16/00; C07K 16/461; C07K 2317/94; C07K 2317/92; C07K 2317/24; C07K 2317/90
See application file for complete search history.

(56) References Cited

U.S. PATENT DOCUMENTS

| | | | |
|---|---|---|---|
| 6,242,190 B1 | 5/2001 | Freire et al. | |
| 7,824,924 B2 | 2/2010 | Trutnau | |
| 8,617,849 B2 | 12/2013 | Schraeml et al. | |
| 8,645,083 B2 | 2/2014 | Schraeml et al. | |

FOREIGN PATENT DOCUMENTS

| | | |
|---|---|---|
| JP | 2005017154 A | 1/2005 |
| JP | 2005513496 A | 5/2005 |
| JP | 2008111713 A | 5/2008 |
| JP | 2008513540 A | 5/2008 |
| WO | 2006/135309 A2 | 12/2006 |
| WO | 2007/018475 A1 | 2/2007 |
| WO | 2007/137984 A2 | 12/2007 |

OTHER PUBLICATIONS

26293 US Questionnaire, 5 pgs.
Barnes et al., "Advances in Animal Cell Recombinant Protein Production: GS-NS0 Expression System" Cytotechnology 32(2):109-23 (Feb. 2000).
Barnes et al., "Characterization of the Stability of Recombinant Protein Production in the GS-NS0 Expression System" Biotechnol Bioeng 73(4):261-70 (May 2001).
Canziani et al., "Kinetic screening of antibodies from crude hybridoma samples using Biacore" Anal Biochem 325(2):301-7 (Feb. 2004).
Carter et al., "Humanization of an Anti-p185 $^{HER2}$ Antibody for Human Cancer Therapy" PNAS 89:4285-4289 (May 1992).
Chaires, "Calorimetry and Thermodynamics in Drug Design" Annu Rev Biophys 37:135-51 (2008).
Dimitrov et al., "Transition Towards Antigen-Binding Promiscuity of a Monospecific Antibody" Mol Immunol. 44:1854-63 (2007).
Drake et al., "Characterizing High-Affinity Antigen/Antibody Complexes by Kinetic- and Equilibrium-Based Methods" Anal Biochem 328(1):35-43 (2004).
Durocher et al., "High-level and High-Throughput Recombinant Protein Production by Transient Transfection of Suspension-Growing Human 293-EBNA1 cells" Nucleic Acids Res 30(2):E9 (2002).
Freire, "Do Enthalpy and Entropy Distinguish First in Class from Best in Class?" Drug Discov Today 13:869-74 (Oct. 2008).
Geisse et al., "Eukaryotic Expression Systems: A Comparison" Protein Expres Purif 8:271-282 (1996).
Gelb, "Microcalorimetric Methods for Peptide Studies" Proceedings of the 4th International Peptide Symposium in conjunction with the 7th Australian Peptide Conference and the 2nd Asia-Pacific International Peptide Symposium, 2007, 1 pg.
Gunnarsson, "Affinity-Based Biosensors for Biomolecular Interaction Analysis" Curr Protoc Immunol (Chapter 18:Unit 18.6.), (2001).
ISA Written Opinion for PCT/EP2010/062115.
James et al., "The Specificity of Cross-Reactivity: Promiscuous Antibody Binding Involves Specific Hydrogen Bonds Rather than Nonspecific Hydrophobic Stickiness" Protein Sci. 12:2183-93 (2003).
Jason-Moller et al. Current Protocols in Protein Science "Overview of Biacore Systems and Their Applications" John Wiley & Sons, Inc, vol. UNIT 19.13 (Supplement 45) (2006).

(Continued)

*Primary Examiner* — Phuong Huynh
(74) *Attorney, Agent, or Firm* — Jonathan P. Aumais (57) ABSTRACT The current invention is directed to the velocity factor. Based on the velocity factor antibodies can be classified, i.e. antibodies can be characterized on their binding properties as e.g. entropic or enthalpic antigen binder. A velocity factor based classification does not require detailed thermodynamic determinations and/or calculations. The velocity factor is the ratio of the antigen-antibody complex association rate constants ka determined at 37° C. and 13° C. As only two experimental determinations are required to calculate the velocity factor this is a fast and high-throughput suited method.

10 Claims, 9 Drawing Sheets

(56) References Cited

OTHER PUBLICATIONS

Kaufman, "Overview of Vector Design for Mammalian Gene Expression" Mol Biotechnol 16:151-160 (2000).

Kikuchi et al., "Determination of Concentration and Binding Affinity of Antibody Fragments by Use of Surface Plasmon Resonance" J Biosci Bioeng 100(3):311-7 (Sep. 2005).

Kohler et al., "Continuous Cultures of Fused Cells Secreting Antibody of Predefined Specificity" Nature 256:495-497 (Aug. 7, 1975).

Leonard et al., "High Throughput Ranking of Recombinant Avian scFv Antibody Fragments from Crude Lysates using the Biacore A100" J Immunol Methods 323(2):172-9 (Jun).

Li et al., "PDBcal: a Comprehensive Dataset for Receptor-Ligand Interactions with Three-Dimensional Structures and Binding Thermodynamics from Isothermal Titration Calorimetry" Chem Biol Drug Des 71(6):529-32 (Jun. 2008).

Liang, "Applications of Isothermal Titration Calorimetry in Protein Science" Acta Biochim Biophys Sin 40(7):565-76 (Jul. 2008).

Makrides, S.C., "Components of Vectors for Gene Transfer and Expression in Mammalian Cells" Protein Express Purif 17:183-202 (1999).

Manivel et al., "The Primary Antibody Repertoire Represents a Linked Network of Degenerate Antigen Specificities" J Immunol. 169(2):888-97 (2002).

Mohan et al., "Association Energetics of Cross-Reactive and Specific Antibodies" Biochem 48:1390-8 (2009).

Norderhaug et al., "Versatile Vectors for Transient and Stable Expression of Recombinant Antibody Molecules in Mammalian Cells" J Immunol Methods 204:77-87 (1997).

Notkins, "Polyreactivity of Antibody Molecules" Trends Immunol 25(4):174-9 (Apr. 2004).

Orlandi et al. et al., "Cloning Immunoglobulin Variable Domains for Expression by the Polymerase Chain Reaction" PNAS USA 86:3833-3837 (May 1989).

Papalia et al., "High-Resolution Characterization of Antibody Fragment/Antigen Interactions using Biacore T100" Anal Biochem. 359:112-9 (2006).

Perozzo et al., "Thermodynamics of Protein-Ligand Interactions: History, Presence, and Future Aspects" J Recept Signal Transduct Res 24(1-2):1-52 (Feb. 2004).

Presta et al. et al., "Generation of a Humanized, High Affinity Anti-Tissue Factor Antibody for Use as a Novel Antithrombotic Therapeutic" Thromb Haemostasis 85(3):379-389 (Mar. 2001).

Rich et al., "Higher-Throughput, Label-Free, Real-Time Molecular Interaction Analysis" Anal Biochem 361(1):1-6 (Feb. 2007).

Roos et al., "Thermodynamic Analysis of Protein Interactions with Biosensor Technology" J Mol Recognit 11(1-6):204-10 (1998).

Safsten et al., "Screening Antibody-Antigen Interactions in Parallel using Biacore A100" Anal Biochem 353(2):181-90 (Jun. 2006).

Sagawa et al., "Thermodynamic and Kinetic Aspects of Antibody Evolution During the Immune Response to Hapten" Mol Immunol. 39:801-8 (2003).

Schlaeger et al., "Transient Gene Expression in Mammalian Cells Grown in Serum-Free Suspension Culture" Cytotechnology 30:71-83 (1999).

Schlaeger, "The Protein Hydrolysate, Primatone RL, is a Cost-effective Multiple Growth Promoter of Mammalian Cell Culture in Serum-containing and Serum-free Media and Displays Anti-apoptosis Properties" J Immunol Methods 194:191-199 (1996).

Steukers et al., "Rapid Kinetic-Based Screening of Human Fab Fragments" J Immunol Methods 310(1-2):126-35 (Mar. 2006).

Tellinghuisen, "Van't Hoff Analysis of K Degrees (T): How Good . . . or Bad?" Biophys Chem 120(2):114-20 (Mar. 2006).

Thielges et al., "Exploring the Energy Landscape of Antibody-Antigen Complexes: Protein Dynamics, Flexibility, and Molecular Recognition" Biochemistry—US 47(27):7237-47 (2008).

Van Regenmortel et al., "Measurement of Antigen-Antibody Interactions with Biosensors" J Mol Recognit 11(1-6):163-7 (1998).

Wark et al., "Latest Technologies for the Enhancement of Antibody Affinity" Adv Drug Deliver Rev 58(5-6):657-670 (Aug. 2006).

Wassaf et al., "High-Throughput Affinity Ranking of Antibodies Using Surface Plasmon Resonance Microarrays" Anal Biochem 351(2):241-53 (Apr. 2006).

Wear et al., "Thermodynamics of the Cyclophilin-A/Cyclosporin-A Interaction: a Direct Comparison of Parameters Determined by Surface Plasmon Resonance Using Biacore T100 and Isothermal Titration Calorimetry" Anal Biochem 359(2):285-7 (Dec. 2006).

Werner et al., "Appropriate Mammalian Expression Systems for Biopharmaceuticals" Arznei-Forschung/Drug Res 48(8):870-880 (1998).

Willuda, J. et al., "High Thermal Stability is Essential for Tumor Targeting of Antibody Fragments: Engineering of a Humanized Anti-Epithelial Glycoprotein-2 (Epithelial Cell Adhesion Molecule) Single-Chain Fv Fragment" Cancer Res 59:5758-5767 (Nov. 15, 1999).

Zhukov et al., "Statistical Aspects of Van't Hoff Analysis: a Simulation Study" J Mol Recognit 20(5):379-85 (2007).

VELOCITY FACTOR

RELATED APPLICATIONS

This application is a divisional of U.S. application Ser. No. 14/090,456, filed Nov. 26, 2013, which is now U.S. Pat. No. 9,488,661, which is a continuation of U.S. application Ser. No. 13/392,217, filed Feb. 24, 2012, which is now U.S. Pat. No. 8,617,849, issued Dec. 31, 2013, which is a national stage entry of International Application No. PCT/EP2010/062115, filed Aug. 19, 2010, which claims the benefit of European Patent Application No. 09010844.0, filed Aug. 25, 2009, the contents of which applications are hereby incorporated by reference in their entirety.

FIELD OF THE INVENTION

The velocity factor is the ratio of the antigen-antibody complex association rate constants determined at 37° C. and 13° C. with which it is possible to classify antibodies e.g. to be an entropic or enthalpic binder without the need of detailed thermodynamic determinations and calculations.

BACKGROUND OF THE INVENTION

The generation of high-affinity antibodies with distinguished antigen specificity and extraordinary antigen complex stability is a major goal in diagnostic and therapeutic antibody development.

Regarding thermodynamic analyses of protein-protein interactions the prevailing technology is the calorimetric assay (Chaires, J. B., Ann. Rev. Biophys. 37 (2008) 135-51; Perozzo, R., et al., J. Recept. Signal Transduct. Res. 24 (1-2) (2004) 1-52; Li, L., et al., Chem. Biol. Drug Des. 71(6) (2008) 529-32; Liang, Y., Acta Biochim. Biophys. Sin. (Shanghai) 40(7) (2008) 565-76; Thielges, M. C., et al., Biochemistry 47(27) (2008) 7237-47). The required sample amount for a reaction calorimeter determination is high, such as an antibody concentration of at least 125 µg/ml and sample volumes of at least 150 µl. Furthermore reaction calorimetry requests high sample purity and does not tolerate any sample impurities or sample heterogeneity. Additionally the sample buffers directly influence the results of the determined thermodynamic parameters. Further, reaction calorimetry is solely able to resolve equilibrium thermodynamics.

Surface Plasmon Resonance (SPR) instrumentation (Roos, H., et al., J. Mol. Recognit. 11(1-6) (1998) 204-210; Van Regenmortel, M. H., et al., J. Mol. Recognit. 11(1-6) (1998) 163-167; Gunnarsson, K., Curr. Prot. Immunol. Chapter 18 (2001) Unit 18.6; Drake, A. W., et al., Anal. Biochem. 328(1) (2004) 35-43; Kikuchi, Y., et al., J. Biosci. Bioeng. 100(3) (2005) 311-7) allows the rapid determination of temperature-dependent kinetic profiles in a high throughput manner (see e.g. Canziani, G. A., et al., Anal. Biochem. 325 (2004) 301-307; Saefsten, P., et al., Anal. Biochem. 353 (2006) 181-190; Leonard, P., et al., J. Immunol. Methods 323 (2007) 172-9).

Wassaf, D., et al. (Anal. Biochem. 351 (2006) 241-253) report high-throughput affinity ranking of antibodies using surface plasmon resonance microarrays. A thermodynamic analysis of protein interactions with biosensor technology is reported in Roos, H., et al., J. Mol. Recognit. 11 (1998) 204-210.

Wark, K. L., et al. (Adv. Drug. Deliv. Rev. 58 (2006) 657-670) report technologies for the enhancement of antibody affinity. High-resolution characterization of antibody fragment/antigen interactions using BIAcore T100 is reported by Papalia, G. A., et al. in Anal. Biochem. 359 (2006) 112-119. Sagawa, T., et al. (Mol. Immunol. 39 (2003) 801-808) report thermodynamic and kinetic aspects of antibody evolution during the immune response to hapten. An overview of BIAcore systems and application is reported by Jason-Moller, L., et al. in Curr. Prot. Prot. Sci. (2006) page unit 19.13. Gelb, W., reports microcalorimetric methods for peptides studies (Proc. 4th Int. Peptide Sympos. (2007) page 1).

SUMMARY OF THE INVENTION

It has been found that for the characterization of antibodies no throughout kinetic characterization is required but furthermore the determination of the association rate constant at 37° C. and the association rate constant at 13° C. is required. The ratio thereof can be used to classify antibodies according to their binding properties.

The first aspect as reported herein is a method for selecting an antibody comprising the step of selecting an antibody with a velocity factor of 10 or less.

In one embodiment the method for selecting an antibody comprises the following steps a) providing a set of or a population or a multitude of antibodies,
b) determining temperature-dependent kinetic data,
c) calculating the velocity factor for all provided antibodies,
d) selecting an antibody with a velocity factor of 10 or less.

In one embodiment the velocity factor is of from 0 to 10. In another embodiment the velocity factor is the ratio of the association rate constant at 37° C. to the association rate constant at 13° C. In still another embodiment the temperature-dependent kinetic data is determined at 13° C. and 37° C. In another embodiment the determining temperature-dependent kinetic data is with surface plasmon resonance. In a further embodiment the method is a high-throughput method. In still another embodiment the selecting is by the velocity factor and by the $\Delta S°‡ass$ value. In one embodiment in the surface plasmon resonance the antigen is immobilized on the surface plasmon resonance chip. In a further embodiment the temperature-dependent kinetic data is thermodynamic equilibrium data and transition state thermodynamic data. In still another embodiment the temperature-dependent kinetic data is calculated with the linear forms of the van't Hoff and Eyring and Arrhenius equations. In one embodiment an antibody is selected with a $\Delta S°‡ass$ of less than 200 J/mol*K ($\Delta S°‡ass < 200$ J/mol*K). In one embodiment an antibody is selected with a $\Delta S°‡ass$ in the range of from −200 J/mol*K to 200 J/mol*K. In also an embodiment an antibody is selected with a $\Delta S°‡ass$ in the range of from −150 J/mol*K to +100 J/mol*K. In another embodiment the surface plasmon resonance is with the HBS-EP buffer supplemented with 1 mg/ml carboxymethyldextrane. In still another embodiment each of the antibodies is produced by a single hybridoma or B-cell.

A second aspect as reported herein is a method for obtaining an antibody with cross-reactivity for at least two antigens comprising selecting an antibody with a velocity factor of 50 or more. In one embodiment the velocity factor is of from 50 to 300.

A further aspect as reported herein is a method for producing an antibody comprising the following steps:

a) providing a set/population/multitude of antibody producing cells, b) selecting an antibody producing cell producing an antibody with a velocity factor of 10 or less,
c) cultivating the selected cell,
d) recovering the antibody from the cultivated selected cell or the cultivation medium thereof and thereby producing an antibody.

In one embodiment the antibody producing cells are deposited as single cells. In a further embodiment the deposited single cells are cultivated prior to the selecting. In another embodiment the antibody is purified prior to the selecting. In a further embodiment the antibody is purified after the recovering. In a specific embodiment the purifying is by Protein A chromatography.

Another aspect as reported herein is a method for selecting a humanized form of a parent antibody comprising
a) providing a parent antibody,
b) providing a set/population/multitude of humanized forms of the parent antibody,
c) determining temperature-dependent kinetic data of all provided antibodies,
d) calculating the velocity factor for all provided antibodies,
e) comparing the velocity factors of the humanized forms with the velocity factor of the parent antibody,
f) selecting a humanized form of a parent antibody by selecting an antibody with a velocity factor that is less than twice of the velocity factor of the parent antibody.

In one embodiment the selecting is of a humanized from with a velocity factor that is less than 125% of the velocity factor of the parent antibody, in another embodiment less than 110% of the velocity factor of the parent antibody.

Still another aspect as reported herein is the use of an antibody selected with a method as reported herein as therapeutic or diagnostic agent. One aspect of the invention is a pharmaceutical composition comprising an antibody obtained with a method as reported herein.

DETAILED DESCRIPTION OF THE INVENTION

The methods reported herein are based on the determination of the velocity factor. Based on the velocity factor antibodies can be classified, i.e. antibodies can be characterized according to their binding properties as e.g. entropic or enthalpic antigen binder. It has been found that a velocity factor based classification does not require detailed thermodynamic to be determined and/or calculated, thus, reducing the amount of parameters to be determined and the number of calculations to be performed. The velocity factor is the ratio of the antigen-antibody complex association rate constants (ka) independently determined at 37° C. and at 13° C. As only two experimental determinations are required to calculate the velocity factor this is a fast and high-throughput suited method.

The velocity factor can be used e.g. to compare a humanized antibody with the parent antibody from which it is derived. It can also be used to evaluate antibodies directly from hybridoma and/or B-cell supernatants. This does not require a preliminary purification as the determination can be made directly with the crude supernatant.

Surface plasmon resonance based kinetic methods have several advantages over conventional calorimetric assays:
high throughput processing is possible,
low sample consumption,
measurement of affinity instead of avidity, and
use of crude cell supernatants or complex cultivation mixtures.

The surface plasmon biosensor surface is an affinity matrix, which is used for example for antibody capturing from crude cell cultivation supernatants. Thus, crude and complex mixtures can be used as samples. As one of the interacting partners is immobilized on the sensor's surface and the second compound is injected into the flow system, the measurement of equilibrium and transition state thermodynamics is possible, as the FIA (Flow Injection Analysis) system allows for and can separately monitor the complex association and dissociation phase.

With this technology the calculation of the thermodynamic parameters
free standard binding enthalpy $\Delta G°$,
standard binding enthalpy $\Delta H°$,
standard binding entropy $\Delta S°$,
and of the transition state parameters
free standard association enthalpy $\Delta G°\ddagger ass$,
standard association enthalpy $\Delta H°\ddagger ass$,
standard association entropy $\Delta S°\ddagger ass$,
activation energy Eaass,
free standard dissociation energy $\Delta G°\ddagger diss$,
standard dissociation enthalpy $\Delta H°\ddagger diss$,
standard dissociation entropy $\Delta S°\ddagger diss$, and
dissociation energy Eadiss
is possible. In case of using the non-linear van't Hoff equation also a $\Delta C_p$ value can be determined.

Generally an SPR-based kinetic antibody screening (see e.g. Steukers, M., et al., J. Immunol. Methods 310 (2006) 126-135; Rich, R. L., et al., Anal. Biochem. 361 (2007) 1-6) is succeeded by a second step of higher resolution thermodynamic SPR analyses.

Antibody producing cell are cultured and the produced cell culture supernatants are subjected to, in one embodiment high throughput, analyses, in which the temperature-dependent kinetic data is generated in order to calculate the velocity factor and transition state (TS) thermodynamic properties. The selection of the antibody according to the method as reported herein is done based on its thermodynamic behavior.

A high affinity antibody is characterized by a temperature-dependent acceleration of the antigen complex association rate constant ka [1/Ms] and a remaining or decelerated antigen complex dissociation rate constant kd [1/s]. Surprisingly, such an antibody is characterized by an antigen interaction mechanism, which shows a large entropy-change in the binding equilibrium. Therefore, a risk assessment must take place by other means than calorimetry to determine from which effect the entropic contribution originates. From the complex association phase, which is risky due to promiscuitive antigen binding, or from the complex dissociation phase, which just indicates a complex antigen interaction, comprising a potentially induced conformational change of the antigen. In one embodiment the entropic contribution comes from the antibody-antigen complex dissociation step, wherein a large positive or a large negative change of the dissociation entropy $\Delta S°\ddagger diss$ takes place.

A high affinity antibody may also have a thermodynamic anomaly originating from the antigen dissociation phase, where the dissociation rate constant kd [1/s] surprisingly and unexpectedly decreases with increasing temperature. Such an antibody is characterized by thermodynamic parameters such as i) a dissociation phase showing a negative or nearby zero dissociation activation energy Eadiss [kJ/mol], ii) a negative dissociation enthalpy $\Delta H°\ddagger diss$ [kJ/mol], and iii) a large negative dissociation entropy $\Delta S°\ddagger diss$ [kJ/mol]. It has to be pointed out that this is a completely theoretical treatment of this effect and shall not be construed as limitation. Thus, in one embodiment the dissociation activation energy Eadiss, the dissociation enthalpy ΔH°‡diss, and the dissociation entropy ΔS°‡diss are determined and an antibody is selected that has i) a negative or nearby zero dissociation activation energy Eadiss [kJ/mol], ii) a negative dissociation enthalpy ΔH°‡diss [kJ/mol], and iii) a large negative dissociation entropy ΔS°‡diss [kJ/mol].

Thus, a method as reported herein allows for the selection of an antibody from a multitude of high affinity antibodies, based on the velocity factor and the ΔS°‡ass value.

Single cell deposited clones can be cultivated prior to screening as in one embodiment in 100 ml spinner culture flasks using RPMI 1640 medium. In another embodiment the antibodies are purified from the supernatant by Protein A Sepharose™ column chromatography prior to the determination of the temperature-dependent kinetic data, i.e. the thermodynamic screening. In one embodiment the system buffer is HBS-EP for the thermodynamic screening. In another embodiment the sample buffer is supplemented with 1 mg/ml carboxymethyldextrane to reduce unspecific sensor matrix effects.

Most publications using SPR-based measurements don't use antibody capture systems as sensor surface presentation technology. Usually the antibody or fragments thereof are covalently immobilized on the sensor. This technology can't be used in a high throughput format, since the surface is not suitable for multi purpose antibody presentation, but it is technically limited by the number of sensors being immobilized with ligands.

Figure 3:
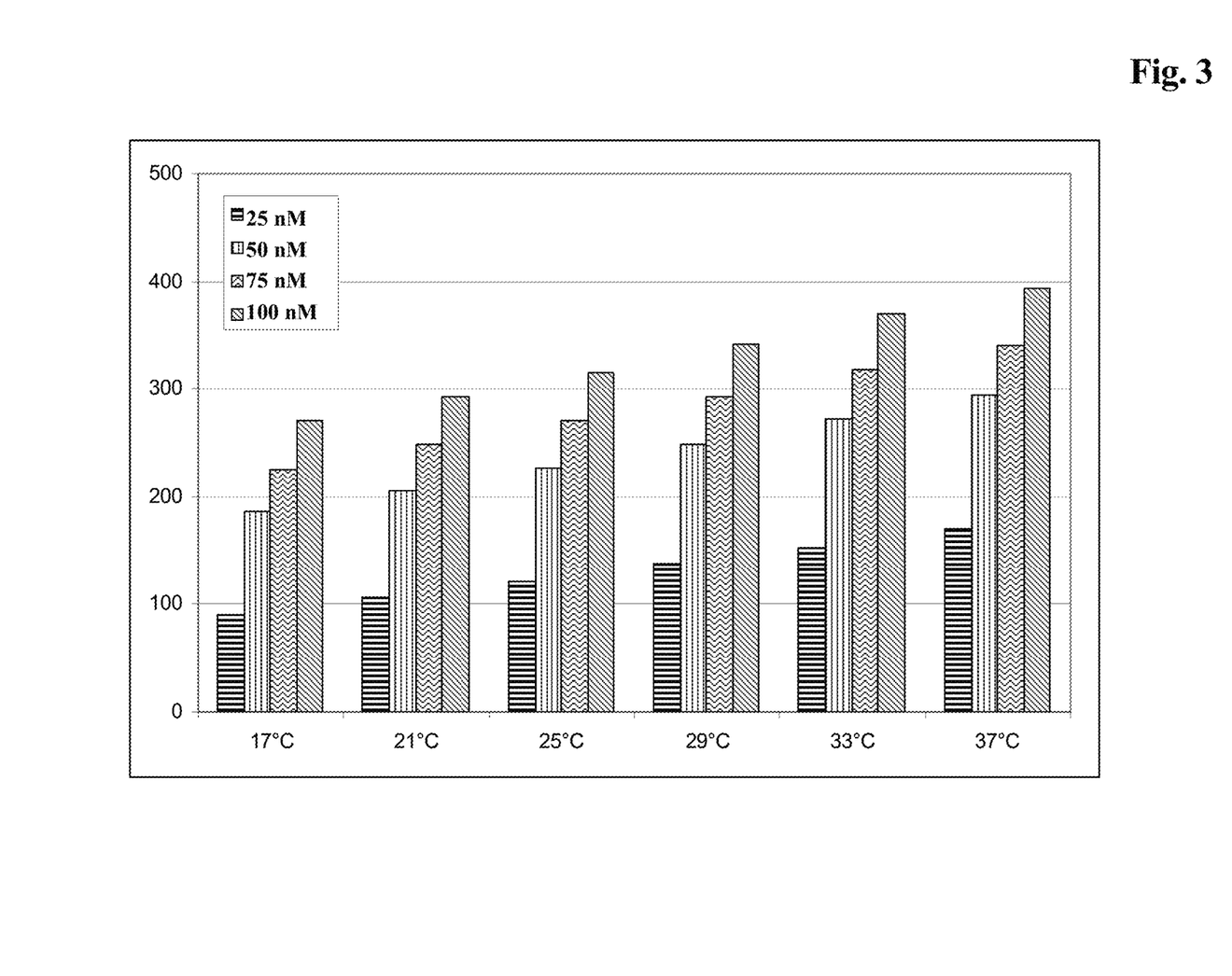
FIG. 3 Secondary antibody response of the <IgGFCγM>R antibody capture system versus the analyte monoclonal antibody at 25 nM, 50 nM, 75 nM and 100 nM and at increasing temperatures.

In order to perform a thermodynamic screening a species specific capture system with appropriate temperature-dependent secondary antibody complex stability can be established. The biosensor has to be calibrated by an optimization procedure to determine the binding characteristics of antibodies with varying epitope specificities in a high throughput format. The thermodynamic screening provides a temperature-dependent set of data (see FIG. 3). At lower temperatures less response is observed, since the capture system's association rate is reduced (see Example 5). At higher temperatures the association rate accelerates.

Further has it been found that at temperatures below 13° C. the capture system's association kinetics are too slow for a sufficient antibody response. Below 13° C. and above 37° C., the antibody's antigen binding kinetics determination provide for non-linearizable data according to the van't Hoff, Eyring and Arrhenius equations.

Figure 5:
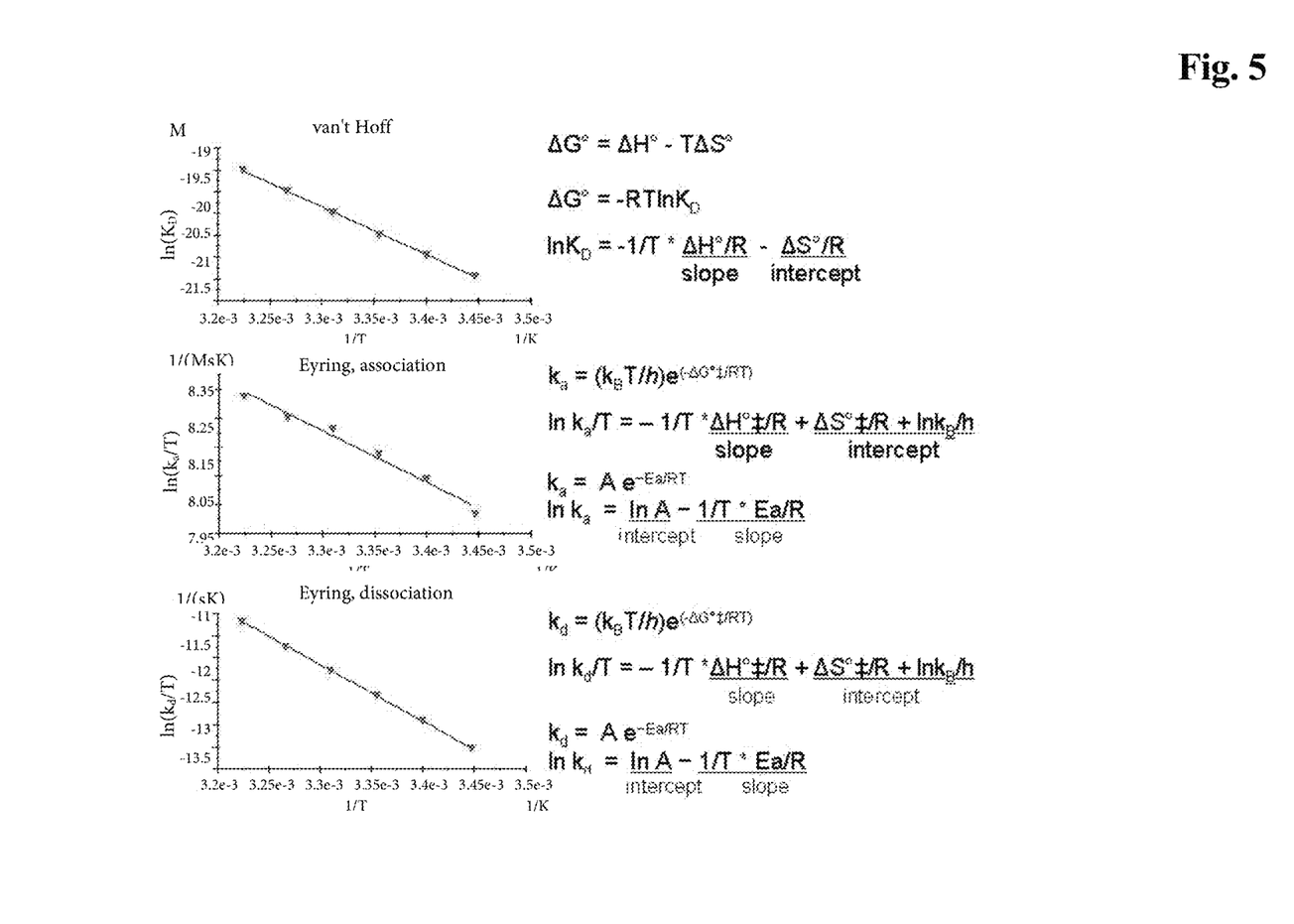
FIG. 5 Calculation of thermodynamic parameters according to the linear equations of (a) van't Hoff, (b) Eyring and (c) Arrhenius. Exemplary plots shown for antibody M D1.1 are shown for the van't Hoff calculation in 5a and for the Eyring calculation in 5b (association) and 5c (dissociation).

In one embodiment the thermodynamic screening is performed at temperatures of 13° C. or 17° C. and 37° C. It has been found that in this temperature range a simple calculation of the thermodynamic equilibrium data according to the linear form of the van't Hoff equation and a simple calculation of transition state thermodynamics according to the linear Eyring and linear Arrhenius equations is possible (Wear, M. A., et al., Anal. Biochem. 359 (2006) 285-287; see also FIG. 5). In one embodiment all measurements are performed under the same conditions in order to make high-throughput-screening (HTS) amenable.

For the calculation the following formulas can be used:

a) Arrhenius equation:

$$k = A * e^{(-Ea/R*T)} \quad (I)$$

b) van't Hoff calculations:

$$\Delta G° = \Delta H° - T*\Delta S° \quad (II)$$

$$\Delta G° = -R*T*\ln K_D \quad (III)$$

$$\ln K_D = -1/T*(\Delta H°/R)/\text{slope} - (\Delta S°/R)/\text{intercept} \quad (IV)$$

$$R*T*\ln K_D = \Delta H°_{T0} - T*\Delta S°_{T0} + \Delta C°_p(T-T_0) - T*\Delta C°_p \ln(T/T_0) \quad (V)$$

c) Eyring association phase:

$$ka = (k_b*T/h)*e^{(-\Delta G°\ddagger/R*T)} \quad (VI)$$

$$\ln ka/T = -1/T*(\Delta H°\ddagger/R)/\text{slope} + (\Delta S°\ddagger*R + \ln k_b/h)/\text{intercept} \quad (VII)$$

$$ka = A*e^{-Ea/R*T} \quad (VIII)$$

$$\ln ka = \ln A/\text{intercept} - (1/T*Ea/R)/\text{slope} \quad (IX)$$

d) Eyring dissociation phase:

$$kd = (k_b*T/h)*e^{(-\Delta G°\ddagger/R*T)} \quad (X)$$

$$\ln kd/T = -1/T*(\Delta H°\ddagger/R)/\text{slope} + (\Delta S°\ddagger/R + \ln k_b/h)/\text{intercept} \quad (XI)$$

$$k_d = A*e^{-Ea/R*T} \quad (XII)$$

$$\ln kd = \ln A/\text{intercept} - (1/T*Ea/R)/\text{slope} \quad (XIII)$$

with
ΔH°—standard binding enthalpy,
ΔS°—standard binding entropy,
ΔG°—free standard binding enthalpy,
T*ΔS°—entropic term,
ΔH°‡ass—standard association binding enthalpy,
ΔS°‡ass—standard association binding entropy,
ΔG°‡ass—standard association free binding enthalpy,
Eaass—Arrhenius Parameter for the association,
ΔH°‡diss—standard dissociation binding enthalpy,
ΔS°‡diss—standard dissociation binding entropy,
ΔG°‡diss—standard dissociation free binding enthalpy,
Eadiss—Arrhenius Parameter for the dissociation,
$K_D$—affinity constant,
ka—association rate constant,
$k_b$—Boltzmann Constant=(1.3806503×10$^{-23}$ m² kg s$^{-2}$ K$^{-1}$),
kd—dissociation rate constant,
h—Planck constant,
$C_p$—molar heat capacity.

The temperature dependency of the free binding enthalpy ΔG° can be calculated for each temperature in the range from 13° C. to 37° C. with the formula ΔG°=−R*T*ln $K_D$. If the value is constant, the linear form of the van't Hoff equation can be used. If ΔG° changes the non-linear form is preferred.

Figure 6:
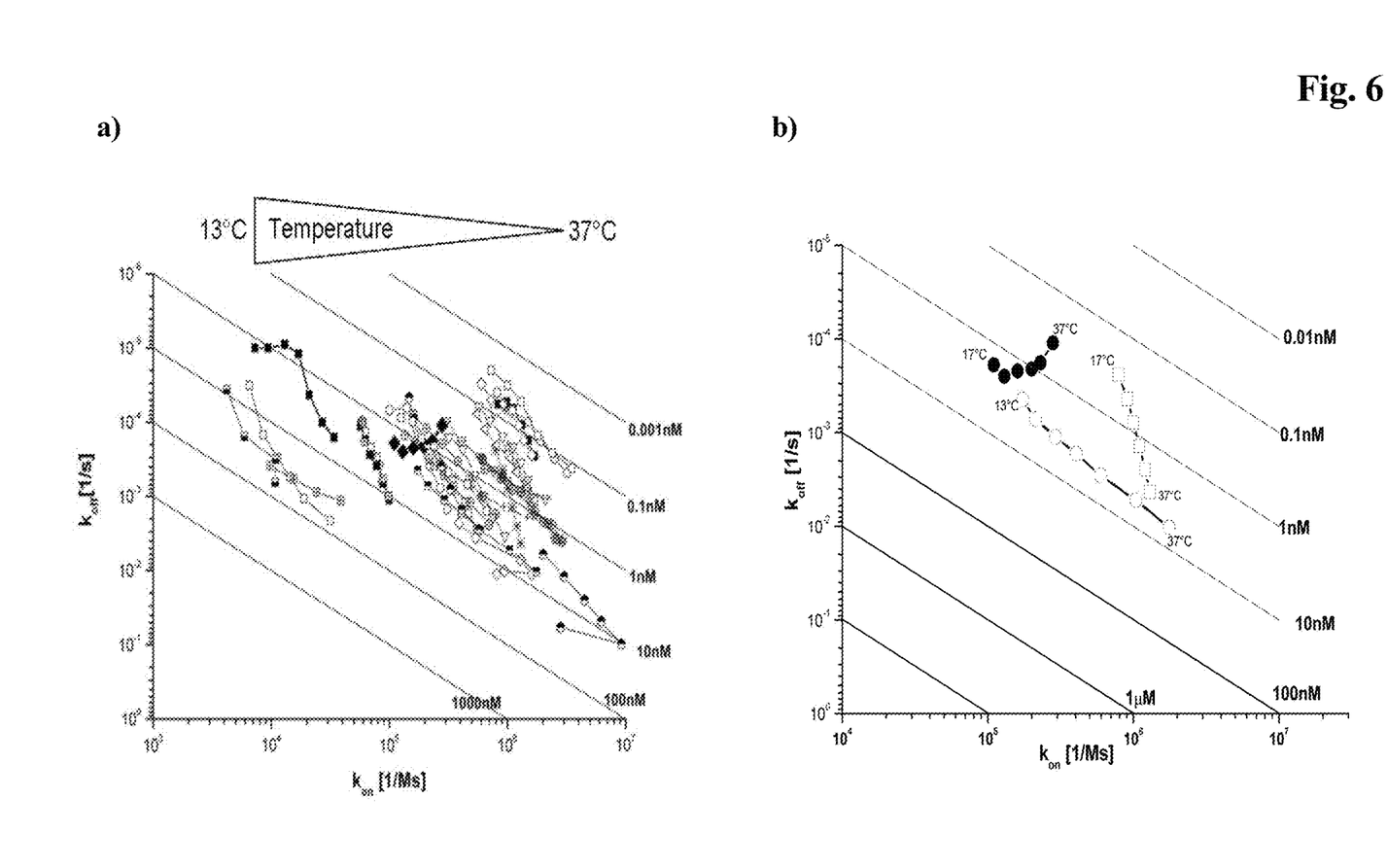

The data obtained in the thermodynamic screening can be visualized in a double logarithmic plot as depicted in FIG. 6 a) wherein the kinetic rate constants ($k_{on}$) ka [1/Ms] and ($k_{off}$) kd [1/s] are denoted on the X- and Y-axis, respectively. Isometric lines (solid lines) indicate areas of the same affinities, which are plotted in bold at the right side of the diagram. Since the ratio of kd/ka provides for the equilibrium constant $K_D$ [M], each data point is equivalent to an affinity at a respective temperature. The arrow above symbolizes the temperature gradient in steps of +4° C. starting at 13° C. or 17° C., respectively, and ending at 37° C. Temperature-dependent affinity trends of each antibody are connected by a line.

Three exemplary affinity trends are shown in FIG. 6 b). In this rate map the $K_D$s in steps of +4° C. of three example antibodies are shown, whereof one is an antibody with increasing affinity with increasing temperature, one is an antibody with constant affinity with increasing temperature, and one is an antibody with decreasing affinity with increasing temperature. Most antibodies show an affinity loss due to lacking antigen complex stability (like those represented by the square in FIG. 6 b)). The affinity remains constant when $k_{on}$ and $k_{off}$ increase (circles). A therapeutic or diagnostic antibody preferably shows an increase in $k_{on}$ and $k_{off}$ with increasing temperature or shows a $k_{on}$ acceleration and a $k_{off}$ deceleration. Likewise the affinity increases and the complex gains stability at higher temperatures (filled circles).

The monitoring of the temperature-dependent kinetics as shown in FIG. 6 is the basis for the selection of antibodies with temperature-independent or temperature-increasing antigen complex stability.

Figure 7:
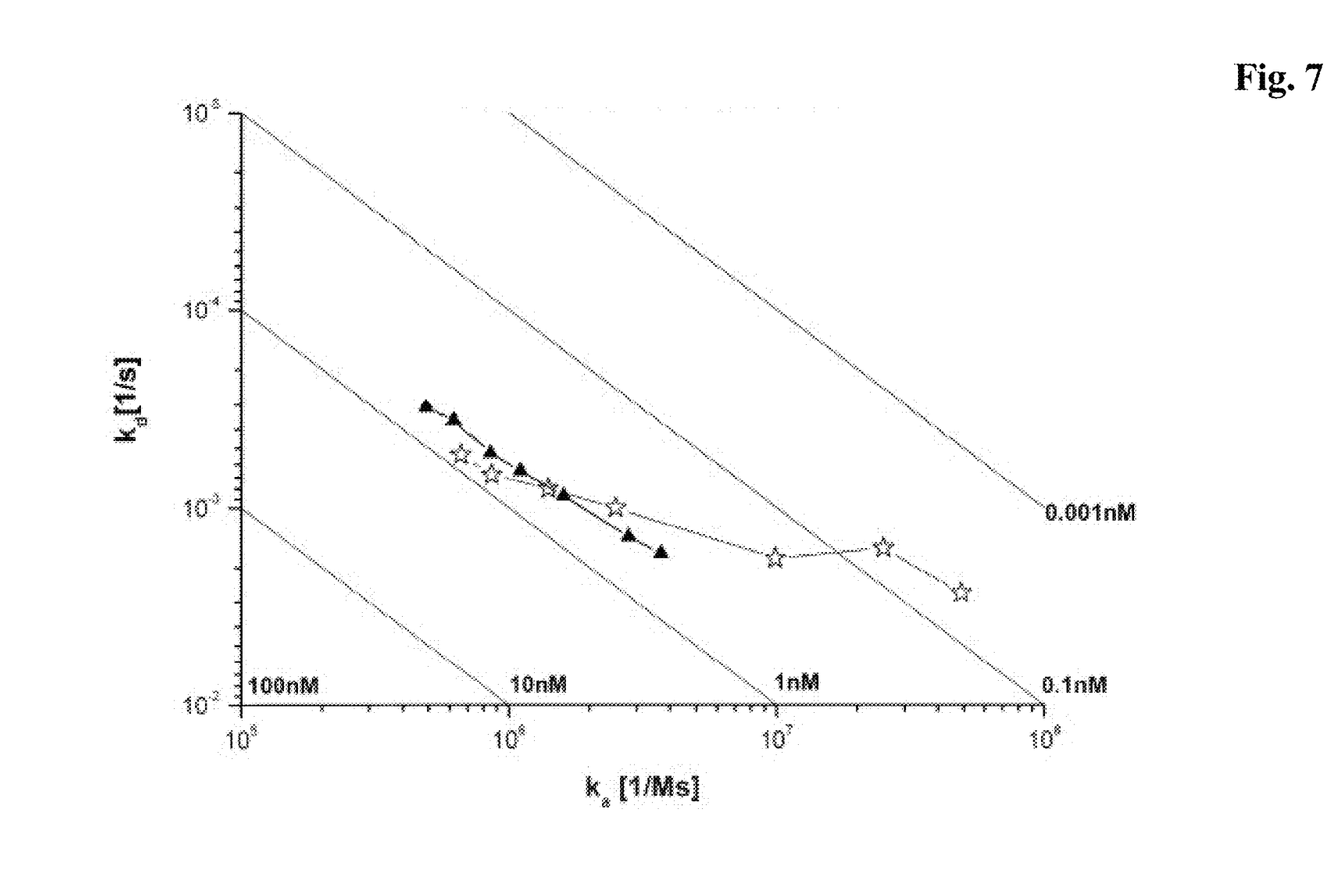
FIG. 7 Rate map with double logarithmical plotting of the antigen dissociation constant kd [1/s] versus the antigen association rate constant ka [1/Ms]; isometric lines indicate areas of constant affinity; the temperature-dependent kinetics of two humanized antibodies, antibody 1 (filled triangles) and antibody 2 (hollow stars) are plotted in the temperature gradient 13° C. to 37° C. in steps of +4° C., beginning at slower association rates at the left of the graphic.

FIG. 7 exemplarily shows two different temperature-dependent kinetics of two antibody forms 1 and 2, which can be obtained in a humanization process. In such a process different combinations of human germline heavy and light chain based sequences can be used to replace murine parental antibody framework sequences. The aim is to select humanized monoclonal antibodies (mAbs) with, preferably, unchanged thermodynamics, specificities and stabilities, when compared to the parental antibody. It can be seen, that antibody 2, in contrast to antibody 1, strongly accelerates its association rate constant ka in the given temperature gradient.

Both antibodies bind the antigen at 37° C. with similar affinity, so that affinity is no suitable selection parameter to discriminate the antibodies.

Since both antibodies strongly differ in their entropic contributions, a much better additional selection parameter is the $\Delta S°\ddagger ass$. For example, the humanized antibody form 1 shows $\Delta S°\ddagger ass=70+/-15$ J/mol*K (Eyring equation, $R^2=0.9601$) and humanized antibody form 2 shows a binding entropy of $\Delta S°\ddagger ass=350+/-70$ J/mol*K (Eyring equation, $R^2=0.9530$). The higher binding entropy of humanized antibody form 2 is reflected by a strong acceleration of the association rate constant ka in the temperature gradient of from 13° C. to 37° C.

It has been found that the acceleration of the antibody-antigen complex formation by a temperature increase, respectively the increase of the association rate constant ka at elevated temperature, correlates with the antibody-antigen association phase entropy $\Delta S°\ddagger ass$.

The antigen-binding interactions of 28 antibodies were thermodynamically quantified. The association phase entropy $\Delta S°\ddagger ass$ and the velocity factor VF (ka(37° C.)/ka (13° C.)) were calculated (see Table 1).

TABLE 1

$\Delta S°\ddagger ass$ of 28 antibodies calculated according to the Eyring equation; all values show $R^2 > 95\%$. SE: error of the calculation.
VF: Velocity Factor.

| antibody | antigen | VF | $\Delta S°\ddagger ass$ [J/mol*K] | SE [J/mol*K] |
|---|---|---|---|---|
| antibody 3 | 4 | 2 | −85 | 7 |
| antibody 4 | 5 | 2 | −53 | 5.1 |
| antibody 5 | 3 | 2 | −77 | 5.4 |
| antibody 6 | 4 | 2 | −73 | 6.9 |
| antibody 7 | 4 | 2 | −83 | 1.2 |
| antibody 8 | 2 | 3 | −18 | 3.5 |
| antibody 9 | 2 | 3 | −10 | 5.8 |
| antibody 10 | 5 | 3 | −66 | 14 |
| antibody 11 | 1 | 2 | −35 | 4.1 |
| antibody 12 | 5 | 2 | −38 | 13 |
| antibody 13 | 1 | 5 | −14 | 1.3 |
| antibody 14 | 2 | 5 | 9 | 6.6 |
| antibody 15 | 1 | 5 | −5.3 | 5.6 |

TABLE 1-continued $\Delta S°\ddagger ass$ of 28 antibodies calculated according to the Eyring equation; all values show $R^2 > 95\%$. SE: error of the calculation.
VF: Velocity Factor.

| antibody | antigen | VF | $\Delta S°\ddagger ass$ [J/mol*K] | SE [J/mol*K] |
|---|---|---|---|---|
| antibody 16 | 1 | 6 | 71 | 23 |
| antibody 17 | 2 | 8 | 77 | 15 |
| antibody 18 | 2 | 9 | 80 | 16 |
| antibody 19 | 2 | 12 | 110 | 29 |
| antibody 20 | 2 | 21 | 160 | 41 |
| antibody 21 | 2 | 74 | 350 | 70 |
| antibody 22 | 2 | 137 | 370 | 78 |
| antibody 23 | 2 | 4 | 6 | 5.5 |
| antibody 24 | 2 | 4 | 3.6 | 4.2 |
| antibody 25 | 2 | 5 | 26 | 9.2 |
| antibody 26 | 6 | 5 | 38 | 13 |
| antibody 27 | 2 | 5 | 24 | 6.3 |
| antibody 28 | 2 | 6 | 34 | 12 |
| antibody 29 | 2 | 6 | 28 | 12 |
| antibody 30 | 6 | 7 | 62 | 14 |
| antibody 31 | 2 | 8 | 77 | 15 |

Table 1 shows data of 28 different murine, human chimeric and humanized murine antibodies, Fab and Fab'2 fragments from murine or human origin, binding to six different antigens. The antigens are all proteinogenous, conformational antigens, differing in their molecular weight. The Velocity Factor VF correlates with $\Delta S°\ddagger ass$, whereby small values of VF correlate with negative or small values for $\Delta S°\ddagger ass$. It has been found that a negative $\Delta S°\ddagger ass$ indicates an enthalpy-driven antibody-antigen interaction, a positive $\Delta S°\ddagger ass$ values indicate entropic/enthalpic interactions and three digit $\Delta S°\ddagger ass$ values stand for fully entropy-driven interactions. Thus, herein is reported a method for selecting a specifically binding antibody comprising the following steps
 a) providing a multitude of antibodies,
 b) determining the association rate constant of each antibody to its antigen at 37° C. and the association rate constant of each antibody to its antigen at 13° C.,
 c) calculating the ratio of the association rate constant at 37° C. to the association rate constant at 13° C.,
 d) selecting a specifically binding antibody by selecting an antibody with a ratio of 10 or less and a $\Delta S°\ddagger ass$ value of 100 J/mol*K or less.

In one embodiment the selecting is of an antibody with a $\Delta S°\ddagger ass$ value of 50 J/mol*K or less.

The higher $\Delta S°\ddagger ass$ the higher is the probability of promiscuitive antibody binding.

Small or negative $\Delta S°\ddagger ass$ correlates to specificity and monospecific binding.

It has been found that it is not necessary to determine association phase thermodynamics by linearizing the data according to the Eyring and Arrhenius equations, where it is the task to produce linearizable high quality data in order to calculate the parameters with acceptable errors. Using the methods as reported herein it is sufficient to determine kinetic data at only two temperatures, i.e. at 13° C. and at 37° C.

Based on the experimental data the values ka(37° C.) and ka(13° C.) are determined by using an appropriate kinetic model. Thereafter the Velocity Factor (VF)=ka(37° C.)/ka (13° C.) is calculated and $\Delta S°\ddagger ass$ is assessed according to the characteristic curve presented in FIG. 8.

Double digit VF-values correlate with three digit $\Delta S°\ddagger ass$ values and indicate a higher risk of promiscuitive binding.

Figure 8:
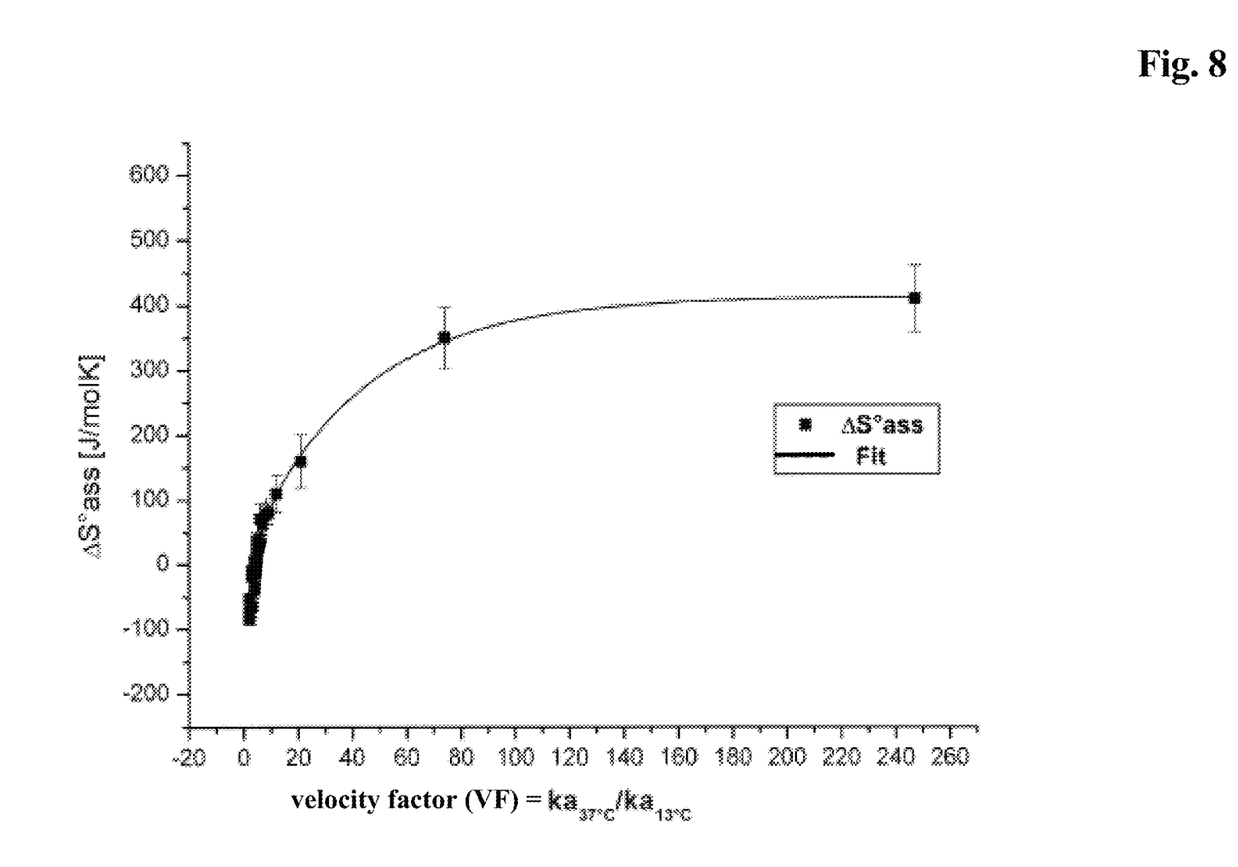
FIG. 8 Data of Table 1. $\Delta S°\ddagger_{ass}$ is plotted versus VF. The data was fitted with an exponential association model according to the equation $y=y0+A1*(1-\exp(x/t1))+A2*(1-\exp(-x/t2))$; $Y0=-185.05789+/-36.83135$; $A1=399.74088+/-36.60886$; $t1=41.93317+/-9.834$; $A2=198.50729+/-29.933$; $t2=3.13298+/-1.32572$; $R^2=0.97575$. The dashed line at VF=10 indicates, that most of the suitable interactions show VF<10.

The data in FIG. 8 were modeled by an exponential association function y=y0+A1*(1−exp(x/t1))+A2*(1−exp(−x/t2)).

According to the graph of the exponential equation, the risk to select an unwanted entropy-driven binder can be minimized. $\Delta S°‡ass$ is estimated by the surrogate parameter VF. In contrast to $\Delta S°‡ass$, VF is an instrumentally easy to access parameter.

FIG. 8 shows that $\Delta S°‡ass$ reaches a plateau value at the equation parameter A1=399.74088+/−36.60886 J/mol*K.

The more relevant data is characterized by small VF values of less than 10 and show smaller standard deviations of $\Delta S°‡ass$.

The fitting parameter A2 (A2=198.50729+/−29.933 J/mol*K) is $\Delta S°‡ass$ at the inflexion of the curve.

Antibodies with $\Delta S°‡ass$ of more than A2 ($\Delta S°‡ass$>A2) are critical, i.e. not well suited, for further processing efforts. FIG. 8 indicates, that most of the antibodies analyzed show VF values of less than 10 (<10). These antibodies can be diagnostically or pharmaceutically used.

Antibodies with $\Delta S°‡ass$ of more than A2, which correlates to a VF of more than 50 show e.g. cross reactivity to further antigens.

Thus, herein is reported a method for selecting a cross-reactive antibody comprising the following steps
  a) providing a multitude of antibodies,
  b) determining the association rate constant of each antibody to its antigen at 37° C. and the association rate constant of each antibody to its antigen at 13° C.,
  c) calculating the ratio of the association rate constant at 37° C. to the association rate constant at 13° C.,
  d) selecting a cross-reactive antibody by selecting an antibody with a ratio of 50 or more and a $\Delta S°‡ass$ value of 200 J/mol*K or more.

In one embodiment the selecting is of an antibody with a $\Delta S°‡ass$ value of 300 J/mol*K or more.

Figure 9:
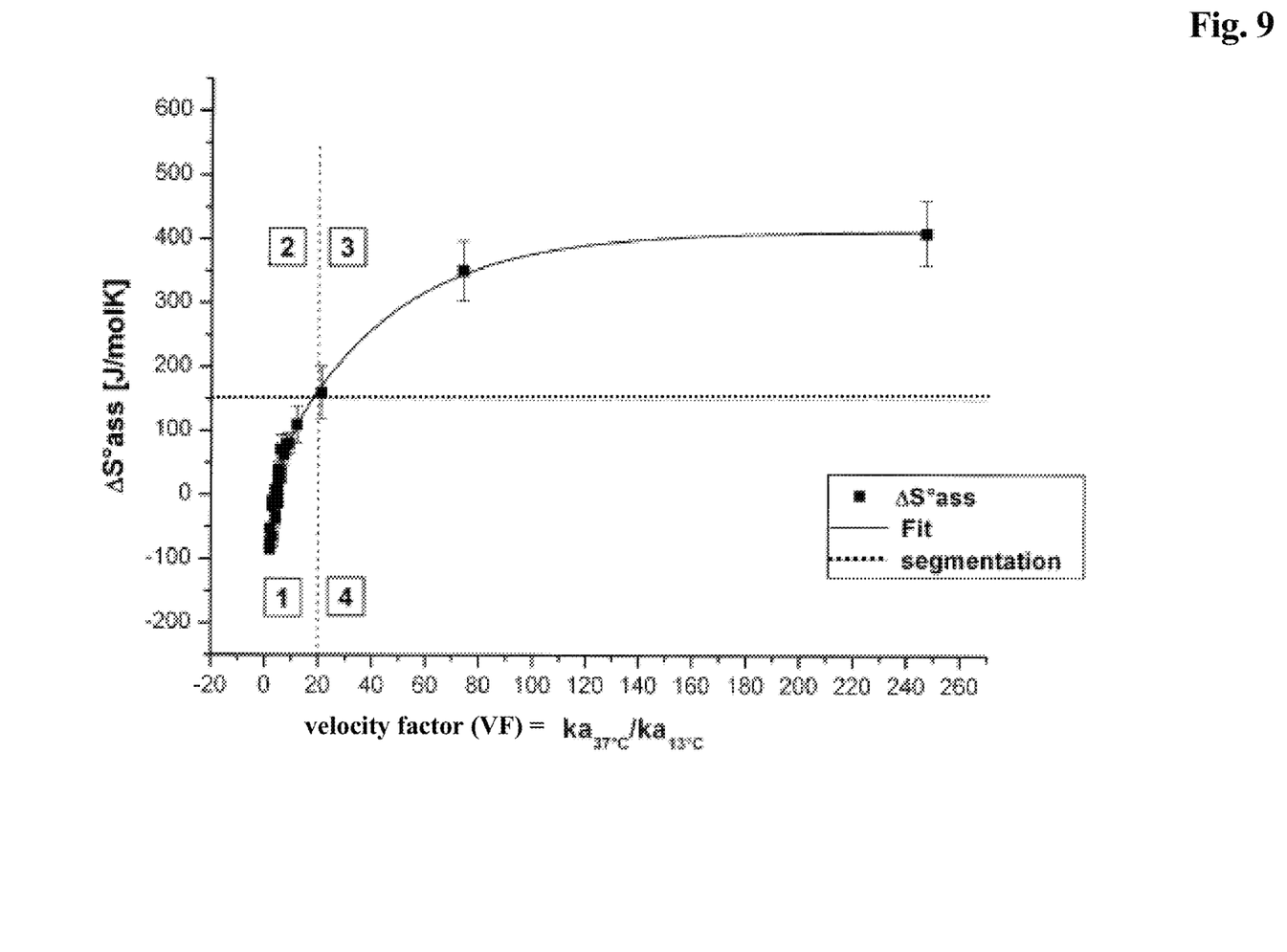
FIG. 9 Segmentation of the plot of FIG. 8 in four corridors by short dotted lines. The segments are numbered 1, 2, 3 and 4.

FIG. 8 can be segmented into four corridors (see FIG. 9). Factors 0<VF<20 indicate a selected screening result. Antibodies in segment 3 show VF factors of more than 20 (VF>20) and are not selected due to their increased $\Delta S°‡ass$ values.

These antibodies are suspicious to promiscuitive antigen binding and require more detailed analyses to clarify the target binding mechanism.

The classification according to FIG. 9 can be used to realize high throughput $\Delta S°‡ass$ based screenings of large antibody populations. For example in the humanization process of antibodies, where the optimal human heavy and light chain compositions are systematically tested for their optimal performance, similar to the parental antibody, the method as reported herein can be used.

The antibodies 8, 9, 17, 18, 20, 21, 22, and 31 as comprised in Table 1 correspond to different stages of a humanization process. From the VF values the process of humanization can be followed. The parental murine antibody 8 shows a low VF value and a negative $\Delta S°‡ass$. The chimeric antibody 9 shows still unchanged VF as well as $\Delta S°‡ass$. The fully humanized antibodies, which are of different VL/VH chain sequence combinations, show discrepancies of VF and therefore of $\Delta S°‡ass$. Finally selected was antibody 31, which shows the lowest VF as well as $\Delta S°‡ass$, whereas antibody 21 and antibody 20 were not selected due to thermodynamic instability, lower functionality in cell culture assays, and/or promiscuitive antigen binding.

Table 1 indicates that the diagram shown in FIG. 9 can also be used for antibody fragments.

The method as reported herein can also be used for obtaining antibodies or antibody producing cells e.g. directly originating from cell mixtures, in one embodiment hybridoma or B-cells, or in another embodiment from a single deposited hybridoma or B-cell, wherein antibodies of potentially inhomogeneous maturation status are excluded, because it is of importance to identify fully mature antibodies with enthalpic binding behavior.

The method as reported herein can be used in high throughput format. Generally, $\Delta S°‡ass$ values are calculated from time-consuming measurements by using a wide-spanning temperature-range and as many data spots as possible in order to get a good linear correlation to calculate transition state parameters according to the Eyring equation with $R^2$>95%.

In the methods as reported herein by using only two temperatures, 13° C. and 37° C., and the reduced kinetic "2 over 2" model precise velocity factors for the association rate can be obtained. This is essential for high throughput $\Delta S°‡ass$ measurements. When combining the high throughput kinetic screening for the identification of highly stable antigen complex forming antibodies with the high throughput determination of the VF factors, best in class antibodies can be selected.

For example, when the VF values in Table 2 are referenced to the $\Delta S°‡ass$/VF diagram it can be seen, that the monoclonal antibody denoted as 1F8 does not show elevated association phase entropy. This has been confirmed also in a different experimental format. The mean VF value of all 16 buffer conditions is 4. The VF value in the reference Table 1 is 4 under similar buffer conditions. This example gives evidence for the applicability of high throughput $\Delta S°‡ass$ analyses by using the VF factors as a $\Delta S°‡ass$ surrogate.

TABLE 2

Matrix showing the Velocity Factors (VF = ka(37° C.)/ka(13° C.)) of the antibody 1F8/antigen interactions for 16 different buffer conditions. All interactions were measured in PBS with varying KCl concentrations and different pH values. Antibody 1F8 would therefore populate segment 1 of FIG. 9.

| 1F8 | pH ↓ | | | | |
|---|---|---|---|---|---|
| KCl [mM] → | | 2.7 | 54 | 162 | 324 |
| | 6.8 | 2 | 4 | 6 | 4 |
| | 7.0 | 4 | 3 | 4 | 3 |
| | 7.4 | 4 | 5 | 4 | 4 |
| | 7.8 | 4 | 4 | 4 | 5 |

The antibody selected with a method as reported herein can be produced recombinantly. Methods for recombinant production of antibodies are known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the respective light and heavy chains can be inserted into expression vectors by standard methods. Expression can be performed in appropriate prokaryotic or eukaryotic host cells like CHO cells, NS0 cells, SP2/0 cells, HEK293 cells, COS cells, PER.C6(R) cells, yeast, or *E. coli* cells, and the antibody can be recovered from the cells (supernatant or cells after lysis). General methods for recombinant production of antibodies are well-known in the state of the art and described, for example, in the review articles of Makrides, S. C., Protein Expr. Purif 17 (1999) 183-202; Geisse, S., et al., Protein Expr. Purif 8 (1996) 271-282;

Kaufman, R. J., Mol. Biotechnol. 16 (2000) 151-160; Werner, R. G., Drug Res. 48 (1998) 870-880.

The term "host cell" as used in the current application denotes any kind of cellular system which can be engineered to generate the antibodies according to the current invention. In one embodiment HEK293 cells and CHO cells are used as host cells. As used herein, the expressions "cell," "cell line," and "cell culture" are used interchangeably and all such designations include progeny. Thus, the words "transformants" and "transformed cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A transient expression system (HEK 293) is reported by Schlaeger, E.-J., and Christensen, K., in Cytotechnology 30 (1999) 71-83 and by Schlaeger, E.-J., in J. Immunol. Methods 194 (1996) 191-199.

The term "specifically binding" denotes the binding of an antibody or Fab fragment with a dissociation constant (=$K_{Diss}$) of at least $10^{-8}$ mol/l or less, i.e. $10^{-9}$ mol/l, or in the range of $10^{-8}$ to $10^{-13}$ mol/l.

The following examples and figures are provided to aid the understanding of the present invention, the true scope of which is set forth in the appended claims. It is understood that modifications can be made in the procedures set forth without departing from the spirit of the invention.

DESCRIPTION OF THE FIGURES

FIG. 4 a) Exemplary concentration-dependent sensogram of the temperature-dependent antibody-antigen interaction of antibody M D1.1. The kinetics were measured in HBS-EP pH 7.4 at 25° C., 3 min. association time, 5 min. dissociation time, fitting according to Langmuir model;

b) Exemplary concentration-dependent sensogram of the temperature-dependent antibody-antigen interaction of antibody M 9.3.1. The kinetics were measured in HBS-EP pH 7.4 at 25° C., 3 min. association time, 15 min. dissociation time, fitting according to a Langmuir 1.1. model.

FIG. 6 a) Double logarithmic plot of the temperature-dependent characteristics of 34 exemplary antibodies;

b) Double logarithmic plot of the temperature-dependent characteristics of three exemplary antibodies: filled circles—antibody with increasing affinity with increasing temperature, open circles—antibody with constant affinity with increasing temperature, squares—antibody with decreasing affinity with increasing temperature.

EXAMPLE 1

Immunization of Mice

Balb/c mice 8-12 weeks old were subjected to intraperitoneal immunization with 100 μg of the antigen formulated as a KLH (keyhole limpet haemocyanine) fusion in complete Freud's adjuvant.

The immunization was performed 4 times: initial boost, 6 weeks, 10 weeks and 14 weeks after the initial boost. The second and third immunization was done using incomplete Freud's adjuvant. The final boost was done i.V. using 100 μg antigen three days before the hybridoma fusion took place. The production of hybridoma primary cultures was done according to Köhler and Milstein (Kohler, G., et al., Nature 256 (1975) 495-497). The hybridomas were isolated in 96-well micro titer plates (MTPs) by limited dilution and were screened for antigen binding by ELISA methods according to the manufacturer's manual. Primary hybridoma cell cultures, which showed a positive color formation upon antigen binding in ELISA, were transferred into the kinetic screening process.

EXAMPLE 2

Preparation of the CM5 Sensor Chip

The BIAcore A100 system under the control of the Software V.1.1 was prepared like follows: A BIAcore CM5 sensor (series S) was mounted into the system and was hydrodynamically addressed according to the manufacturer's recommendations.

In case of analyzing a murine antibody, the polyclonal rabbit anti-IgG antibody <IgGFCγM>R (Jackson ImmunoResearch Laboratories Inc.) was immobilized on the flow cells via EDC/NHS chemistry according to the manufacturer's instructions.

In case of using human chimeric or fully humanized antibodies, the polyclonal goat antibody pAb<h-lgG, Fcg-Frag>G-IgG(IS) (Jackson ImmunoResearch Laboratories Inc.) was immobilized on all flow cells via EDC/NHS chemistry according to the manufacturer's instructions.

In case of using murine IgG Fab or Fab'2 fragments, the polyclonal goat antibody <MFab>G-IgG(IS) (Bethyl L. Cat. No. A90-100A-5 v. 9.8.2000) was immobilized on all flow cells via EDC/NHS chemistry according to the manufacturer's instructions.

In case of using human or humanized IgG Fab or Fab'2 fragments, the polyclonal goat antibody <huFab'2>G-IgG (Jackson Immuno Research Laboratories Inc.) was immobilized on all flow cells via EDC/NHS chemistry according to the manufacturer's instructions.

EXAMPLE 3

Kinetic Screening of Primary Hybridoma Culture Supernatants

Hybridoma culture supernatants from different immunization campaigns conducted according to Example 1 were processed as outlined below.

The spots 2 and 4 of a sensor chip obtained according to Example 2 were used as a reference (1-2, 5-4). In order to capture antibody on the sensor surface hybridoma culture supernatants were diluted 1:5 with running buffer HBS-EP (10 mM HEPES pH 7.4, 150 mM NaCl, 1 mM EDTA, 0.05% P20, BIAcore) and were injected at 30 µl/min. for 1 min. Subsequently, the respective antigen was injected at 30 µl/min. for 2 to 3 min. association time. The dissociation phase was monitored for 5 to 15 min. Finally the surface was regenerated with a 2 min. injection of 100 mM phosphoric acid.

The sensor was preconditioned by repeated cycles of antibody capturing and regeneration.

Figure 1:
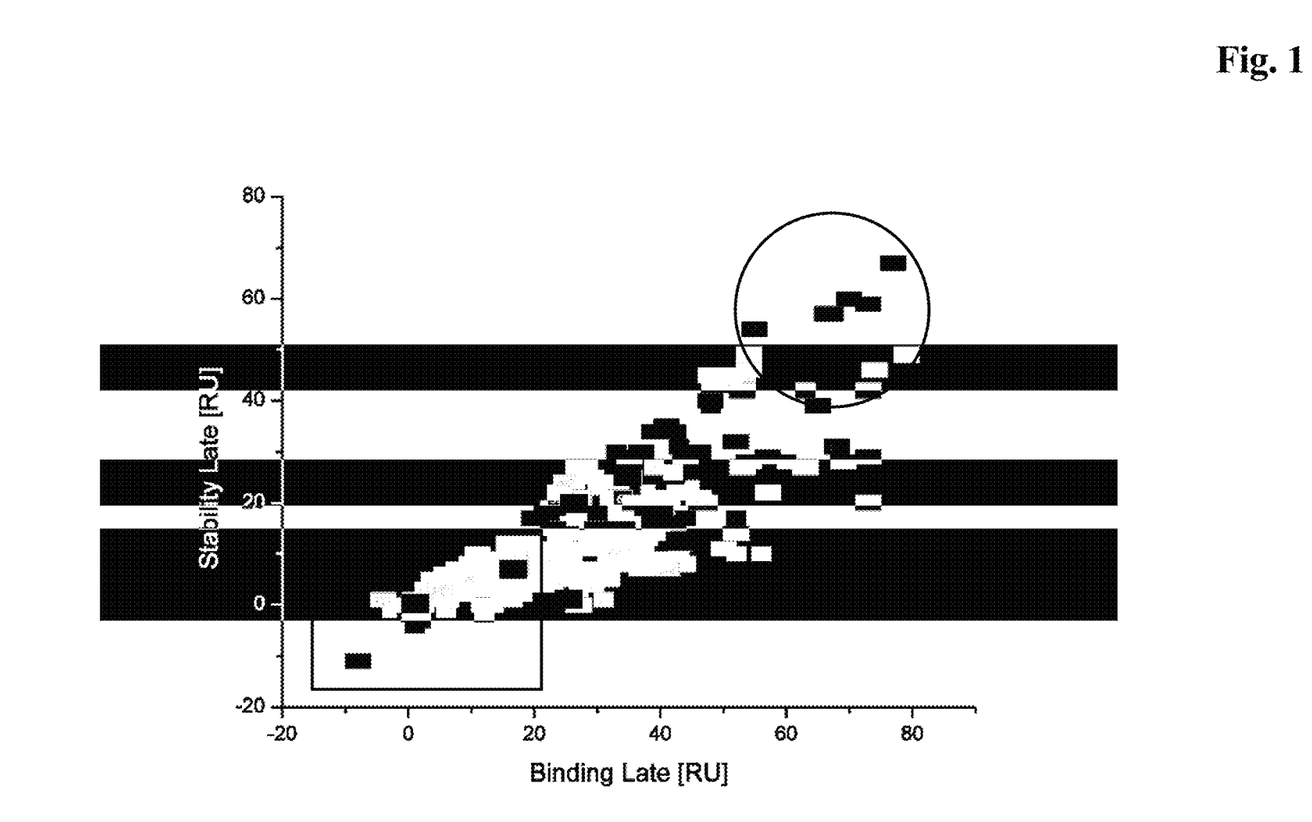
FIG. 1 Illustration of the Binding Late (BL) and Stability Late (SL) data of exemplary antibodies.

For the selection of primary hybridomas the following procedure was used: A Binding Late (BL) reference point was set shortly before the antigen's injection ended. A Stability Late (SL) reference point was set shortly before the end of the complex dissociation phase. The BL and SL data were graphically visualized (FIG. 1). The data was used to calculate the antigen complex stability using formula (XIV):

$$(1-[BL(RU)-SL(RU)/BL(RU)]) \quad \text{(XIV)}$$

Figure 2:
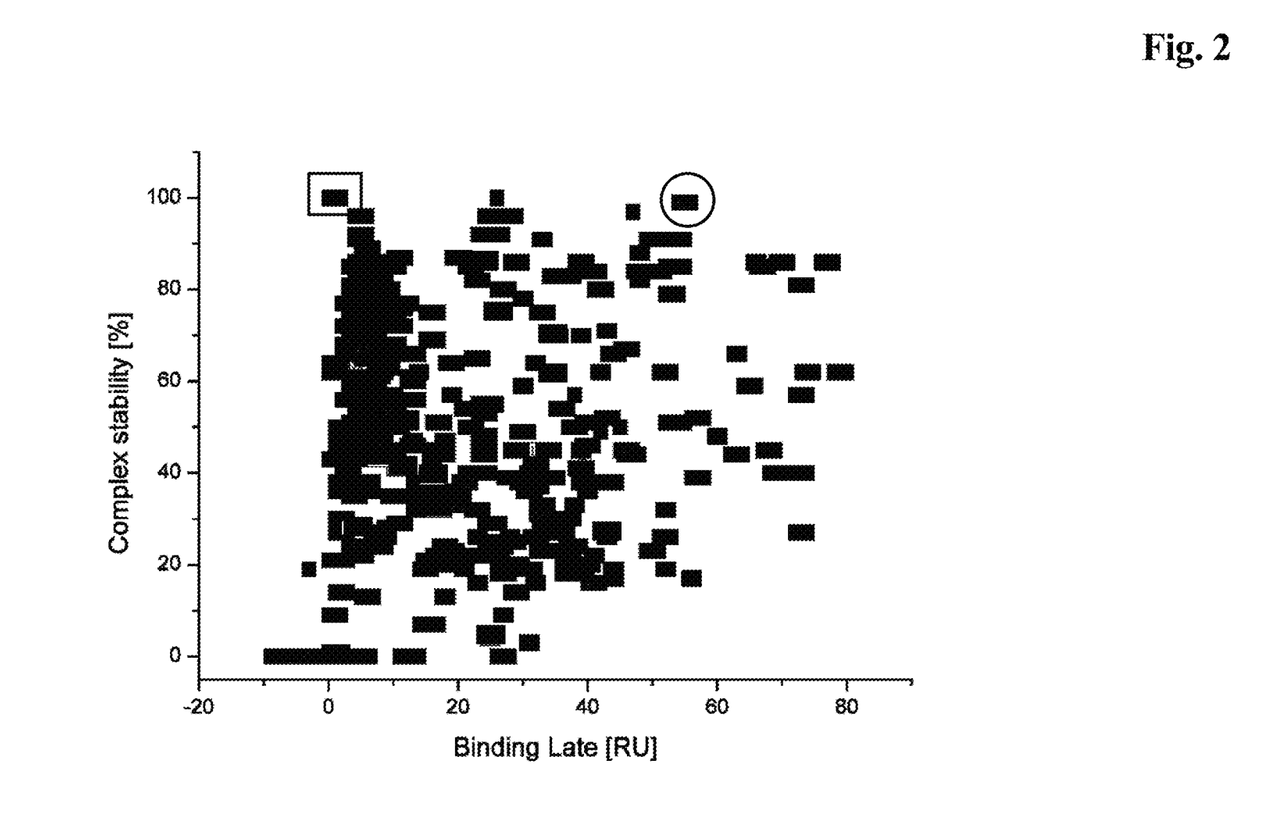
FIG. 2 Binding Late/Complex Stability plot of 549 hybridoma primary cultures: the encircled data spot shows sufficient antigen response signal and 100% complex stability, whereas the enframed data spot shows no sufficient antigen response.

(see FIG. 2). E.g. the encircled data spots show sufficient antigen response signal and 100% complex stability, whereas the enframed data spot shows no sufficient antigen response.

Thus, the top 10% hybridomas according to antigen response signal and complex stability have been selected.

EXAMPLE 4

Hybridoma Cloning and Antibody Production

Antibody producing hybridoma primary cultures selected according to Example 3 were subcloned using the cell sorter FACSAria (Becton Dickinson) under the control software V4.1.2. The deposited single clones were incubated under suitable conditions for further proliferation in 24 well plates and were subsequently transferred to the thermodynamic screening process according to Example 5 after having determined the antibody concentration in solution using ELISA methods according to the instruction of the manufacturer.

EXAMPLE 5

Thermodynamic Screening

Secreted antibodies were characterized by a thermodynamic screening employing the determination of the temperature-dependent kinetics in order to determine the antigen-antibody complex thermostability and in order to calculate thermodynamic properties.

A CM5 sensor series S was mounted into the BIAcore T100 System driven under the control software V1.1.1 and preconditioned by 1 min. injection at 100 µl/min. of a mixture comprising 0.1% SDS, 50 mM NaOH, 10 mM HCl and 100 mM $H_3PO_4$.

In case of analyzing a murine antibody, the polyclonal rabbit anti-IgG antibody <IgGFCgammaM>R (Jackson ImmunoResearch Laboratories Inc.) was immobilized on the flow cells via EDC/NHS chemistry according to the manufacturer's instructions.

In case of using human chimeric or fully humanized antibodies, the polyclonal goat antibody pAb<h-IgG, Fcg-Frag>G-IgG(IS) (Jackson ImmunoResearch Laboratories Inc.) was immobilized on all flow cells via EDC/NHS chemistry according to the manufacturer's instructions.

In case of using murine IgG Fab or Fab'2 fragments, the polyclonal goat antibody <MFab> G-IgG(IS) (Bethyl L. Cat. No. A90-100A-5 v. 9.8.2000) was immobilized on all flow cells via EDC/NHS chemistry according to the manufacturer's instructions.

In case of using human or humanized IgG Fab or Fab'2 fragments, the polyclonal goat antibody <huFab'2>G-IgG (Jackson Immuno Research Laboratories Inc.) was immobilized on all flow cells via EDC/NHS chemistry according to the manufacturer's instructions.

The concentration values of the reference antibody were adjusted in order to achieve similar secondary antibody response levels at different temperatures.

Figure 4:
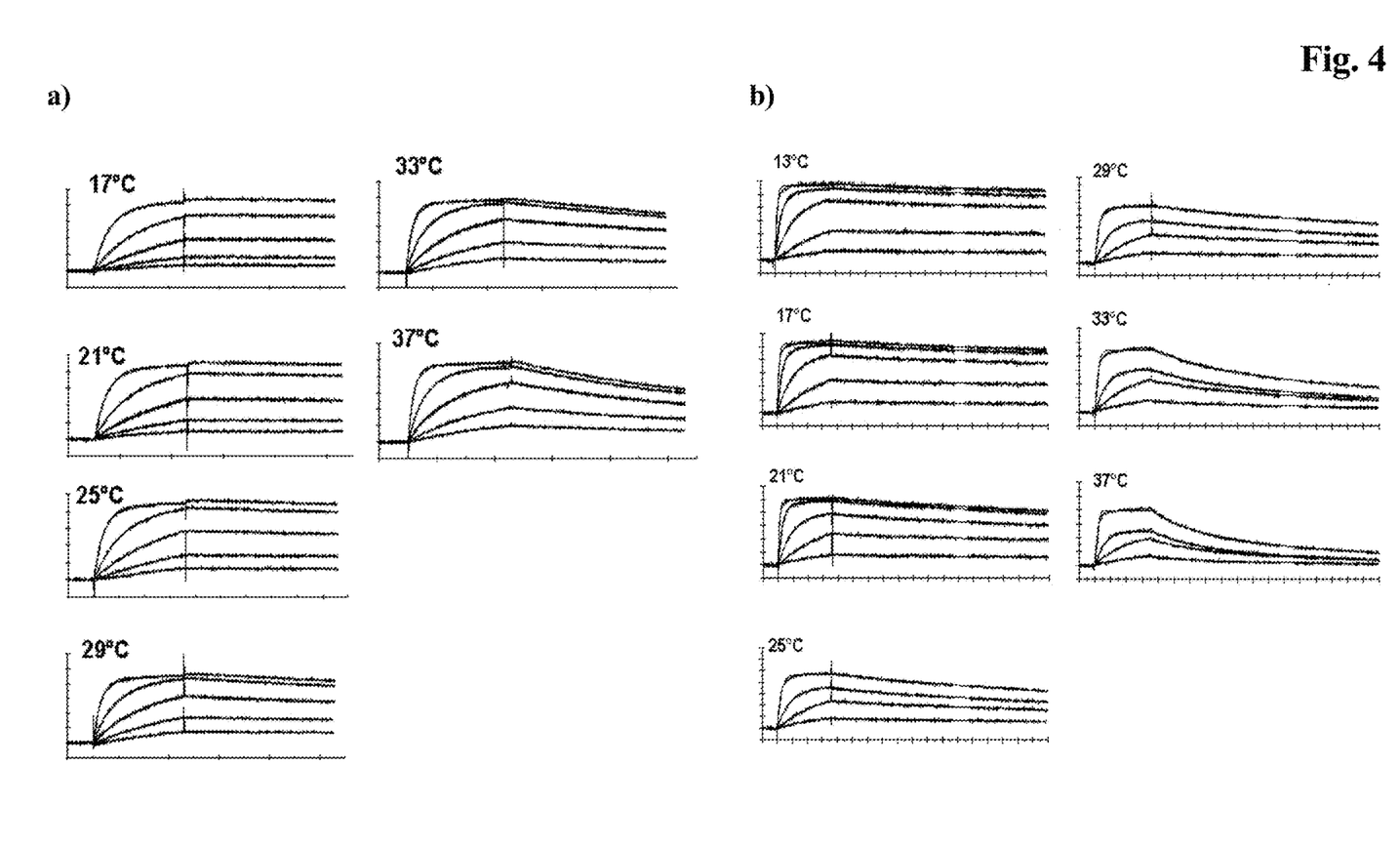

Kinetic measurements at different temperatures were performed at 20 µl/min., the flow rate was 30 µl/min., 50 µl/min., 100 µl/min., respectively. The sample injection of the antigen was done for 30 sec., 90 sec., 180 sec., respectively, or other suitable injection times in order to achieve ligand saturation or entry into the binding equilibrium during the complex association phase (see FIG. 4 a)). The dissociation rate was monitored first for up to 300 sec. and further for 15 min. (see FIG. 4 b)). The antigen injections were repeated in different concentration steps of at least five concentrations. As control one concentration step was analyzed twice to control the reproducibility of the assay. Flow cell 1 served as a reference. A buffer injection was used instead of an antigen injection to double reference the data by buffer signal subtraction. The capture system was regenerated using 100 mM $H_3PO_4$ by a 2 min. injection at 100 µl/min. The regeneration procedure was optimized to guarantee quantitative surface regeneration also at 13° C., 17° C. and 21° C. At these temperatures the regeneration solution was injected three times whereas at 25° C., 29° C., 33° C. and 37° C. the regeneration solution was injected one time.

The data obtained was evaluated according to a 1:1 binary Langmuir interaction model in order to calculate the association rate constant ka [1/Ms], the dissociation rate constant kd [1/s] and the resulting affinity constant $K_D$ [M] at different temperatures. Thermodynamic equilibrium data was calculated according to the linear form of the Van't Hoff equation. Transition State thermodynamics were calculated according to the Eyring and Arrhenius equations using e.g. the BIAcore T100 evaluation software V.1.1.1 or the program Origin 7SRI v. 7.0300.

EXAMPLE 6

Example for the Effect of the Adjustment to Homogeneous $RU_{MAX}$ Values

A BIAcore T100 device was mounted with a CM5 series-S BIAcore sensor, and was immobilized with 6000 RU <IgGFCγM>R (Jackson ImmunoResearch Laboratories Inc., USA) on each flow cell according to the manufacturer's instructions. The non-optimized experiment used 40 nM capture antibody at 20 µl/min., in HBS-EP buffer (0.05% P20). The sample buffer was the system buffer, supplemented with 1 mg/ml CMD (carboxymethyldextrane).

The antigen was injected after the capturing of the secondary antibody in six concentration steps of 1.2 nM, 4 nM, 11 nM, 33 nM, 100 nM and 300 nM, whereby 11 nM were used as a double control and 0 nM were used as reference. The antigen was injected at 100 µl/min. for 2 min. association and 5 min. dissociation, followed by a HBS-EP wash of 15 min. at 30 µl/min. and a regeneration with 10 mM glycine pH 1.7 at 3 µl/min. for 3 min. Concentration-dependent measurements were done at 4° C., 11° C., 18° C., 25° C., 32° C., and 40° C.

The optimized system was used like described above, but with the exceptions that the antibody to be captured was injected for 3 min. association time at different concentration steps of 100 nM at 15° C., 80 nM at 20° C., 60 nM at 25° C., 50 nM at 30° C., 40 nM at 35° C. and 40 nM at 40° C.

Finally kinetics and thermodynamics were determined using the BIAcore evaluation software.

EXAMPLE 7

Determination and Calculation of the Velocity Factor

A CM5 sensor series S was mounted into the BIAcore T100 System.

In case of using murine antibodies, the polyclonal rabbit IgG antibody <IgGFCγM>R (Jackson ImmunoResearch Laboratories Inc.) was immobilized on the flow cells via EDC/NHS chemistry according to the manufacturer's instructions.

In case of using human chimeric or fully humanized antibodies, the polyclonal goat antibody pAb<h-lgG, Fcg-Frag>G-IgG(IS) (Jackson ImmunoResearch Laboratories Inc.) was immobilized on all flow cells via EDC/NHS chemistry according to the manufacturer's instructions.

In case of using murine IgG Fab or Fab'2 fragments, the polyclonal goat antibody <MFab>G-IgG(IS) (Bethyl L. Cat. No. A90-100A-5 v. 9.8.2000) was immobilized on all flow cells via EDC/NHS chemistry according to the manufacturer's instructions.

In case of using human or humanized IgG Fab or Fab'2 fragments, the polyclonal goat antibody <huFab'2>G-IgG (Jackson Immuno Research Laboratories Inc.) was immobilized on all flow cells via EDC/NHS chemistry according to the manufacturer's instructions.

The sample buffer was the system buffer supplemented with 1 mg/ml carboxymethyldextrane to reduce unspecific sensor matrix effects. Kinetic measurements in the temperature gradient 13° C. to 37° C. were performed at 100 µl/min.

The analyte injections of recombinant synthetic human full length antigen 1, recombinant human antigen 2 (10 kDa), recombinant human antigen 3 human FC-chimera (R&D Systems, 160 kDa), recombinant human antigen 4 (29 kDa), or recombinant human antigen 5 (72 kDa) were done for 180 sec. The dissociation rate was monitored for up to 900 sec. The antigen injections were repeated in different concentration steps of at least five concentrations. As a control one concentration step was analyzed twice to control the reproducibility of the assay. Flow cell 1 was used as reference. A blank buffer injection was used instead of an antigen injection to double reference the data by buffer signal subtraction.

Prior to each assay, homogenous $RU_{MAX}$ values in the temperature range 13° C.-37° C. were adjusted by titration experiments with the respective antibodies to be presented on the sensor surface (see section in which the temperature-dependent titration experiments are described in detail). The kinetics were measured in the temperature gradient 13° C., 17° C., 21° C., 25° C., 29° C., 33° C. and 37° C. The capture systems were regenerated using a buffer wash with HBS-ET buffer at 30 µl/min. for 15 sec., prior to regeneration with 10 mM glycine pH 1.5 at 30 µl/min. for 15 sec., followed by a 1 min. injection and a 30 sec. injection of 10 mM glycine at pH 1.7.

The data obtained was evaluated according to a 1:1 binary Langmuir interaction model in order to calculate the association rate constants ka [1/Ms], the dissociation rate constants kd [1/s] and the resulting affinity constants $K_D$ [M] at the respective temperatures. Thermodynamic equilibrium data was calculated according to the linear and non linear form of the Van't Hoff equation. Transition State thermodynamics were calculated according to the Eyring and Arrhenius equations using e.g. the BIAcore T100 evaluation software V.1.1.1. Graphic evaluation was done using Origin 7SRI v. 7.0300.

The Velocity Factor (VF) was calculated as the quotient of the antigen complex association rates ka (1/Ms) at 37° C. and 13° C. The exponential association fitting curve $y=y0+A1*(1-\exp(x/t1))+A2*(1-\exp(x/t2))$ was used.

EXAMPLE 8

High Throughput Velocity Factor Analysis

A CM5 sensor series S was mounted into the BIAcore A100 System and the detection spots were hydrodynamically addressed according to the manufacturer's instructions.

The polyclonal rabbit IgG antibody <IgGFCγM>R (Jackson ImmunoResearch Laboratories Inc.) was immobilized at 4 kRU on the detection spots 1 and 5 in each flow cell. 800 RU <IgGFCγM>R were immobilized on spots 2 and 4 in each flow cell. Coupling was done via EDC/NHS chemistry according to the manufacturer's instructions. The sample buffer was the system buffer supplemented with 1 mg/ml carboxymethyldextrane to reduce unspecific sensor matrix effects.

The basic buffer system was PBS (phosphate buffered saline). The buffer was adjusted to four different pH conditions: pH 6.8, pH 7.0, pH 7.4 and pH 7.8, and four different KCl concentrations: 2.7 mM, 54 mM, 162 mM and 324 mM. Sixteen different sample buffer conditions were tested.

The mAbs to be captured were injected at 10 µl/min. for 1 min. at different concentration steps between 60 nM at 37° C. and 240 nM at 13° C. to ensure homogenous $RU_{MAX}$ values in the subsequent antigen interaction measurements.

Kinetic measurements in the temperature gradient 13° C. to 37° C. were performed at 30 µl/min. The analyte injections of recombinant human antigen 1-84 (9.4 kDa), were done for 180 sec. The dissociation rate was monitored for 600 sec. The antigen injections were repeated in two concentration steps at 60 nM and 240 nM. A blank buffer injection was used instead of an antigen injection to double reference the data by buffer signal subtraction.

The capture system was regenerated using a 15 sec. buffer wash with HBS-ET buffer at 30 µl/min., prior to regeneration with 10 mM glycine pH 1.5 at 30 μl/min. for 90 sec., followed by 2×30 sec. injection of the same buffer.

The kinetic data obtained was evaluated according to a "2 over 2" kinetic model, which uses two different ligand densities of the sensor matrix to calculate kinetics by just using two antigen concentrations. The association rate constants ka [1/Ms], the dissociation rate constants kd [1/s] and the resulting affinity constants KD [M] at the respective temperatures were calculated using the BIAcore A100 evaluation software 1.1.

Thermodynamic equilibrium data was calculated from the kinetic data according to the linear form of the Van't Hoff equation. Transition State thermodynamics were calculated according to the Eyring equations using Excel. Graphic evaluation was done using Origin 7SRI v. 7.0300. The Velocity Factor (VF) for the association phase was calculated as the quotient of the antigen complex association rates ka (1/Ms) at 37° C. and 13° C. The Velocity Factor for the dissociation rates were calculated as the quotient of kd (1/s) at 13° C. and 37° C.

The invention claimed is:

1. A method for obtaining a humanized antibody comprising:
   a) providing a parent antibody,
   b) providing a set of humanized forms of the parent antibody,
   c) measuring the association rate constant for each humanized antibody form to its antigen at 37° C. and at 13° C.,
   d) calculating the velocity factor for the provided antibodies,
   e) comparing the velocity factor of the humanized forms with the velocity factor of the parent antibody, and
   f) selecting a humanized form of the parent antibody as the humanized antibody with a velocity factor that is less than twice the velocity factor of the parent antibody and thereby obtaining the humanized antibody;
   wherein the velocity factor of an antibody is a ratio of its Ka(37° C.)/Ka(13° C.).

2. The method according to claim 1, wherein the association rate constant is measured using a surface plasmon resonance assay.

3. The method according to claim 1, wherein the selection of the antibody is further selected by determining $\Delta S°‡ass$.

4. The method according to claim 2, wherein for the surface plasmon resonance assay, the antigen is immobilized on the surface plasmon resonance chip.

5. The method according to claim 3, wherein the antibody is selected with a $\Delta S°‡ass$ of less than 200 J/mol*K.

6. The method according to claim 5, wherein the $\Delta S°‡ass$ is less than 125% of the $\Delta S°‡ass$ of the parent antibody.

7. The method according to claim 6, wherein the $\Delta S°‡ass$ is less than 110% of the $\Delta S°‡ass$ of the parent antibody.

8. The method according to claim 1, wherein the parent antibody is produced by a single hybridoma or B-cell.

9. The method according to claim 6, wherein the velocity factor is less than 1.25.

10. The method according to claim 6, wherein the velocity factor is less than 1.10.

* * * * *